United States Patent [19]

McDonald

[11] Patent Number: 4,959,070
[45] Date of Patent: Sep. 25, 1990

[54] INTRAOCULAR LENS IMPLANTATION

[76] Inventor: Henry H. McDonald, 65 N. Madison, Suite 810, Pasadena, Calif. 91101

[21] Appl. No.: 302,209

[22] Filed: Jan. 27, 1989

Related U.S. Application Data

[63] Continuation of Ser. No. 42,881, Apr. 27, 1987, Pat. No. 4,813,957.

[51] Int. Cl.$^5$ .......................... A61F 2/16; A61B 17/28
[52] U.S. Cl. ......................................... 623/6; 606/107
[58] Field of Search ...................... 128/321, 354, 325; 623/6; 606/107

[56] References Cited

U.S. PATENT DOCUMENTS

| | | | |
|---|---|---|---|
| 119,055 | 9/1918 | Shanerer | 128/321 |
| 1,837,277 | 12/1931 | Lund | 128/321 |
| 3,980,086 | 9/1976 | Kletschka | 128/321 |
| 4,573,998 | 3/1986 | Mazzocco | 128/321 |
| 4,785,810 | 11/1988 | Baccala | 128/321 |
| 4,844,065 | 7/1989 | Faulkner | 606/107 |

FOREIGN PATENT DOCUMENTS 361627  5/1921  Fed. Rep. of Germany ...... 128/321

Primary Examiner—Randall L. Green
Assistant Examiner—David H. Willse
Attorney, Agent, or Firm—William W. Haefliger

[57] ABSTRACT

Intraocular lens implantation is achieved via a very small incision in the corneo-scleral limbus of the eye.

2 Claims, 4 Drawing Sheets

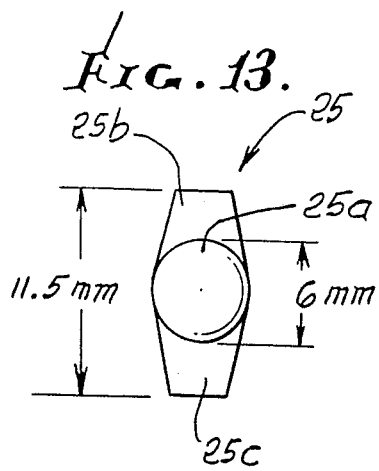
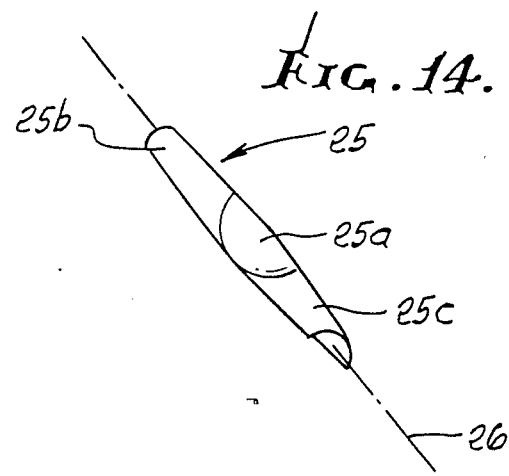
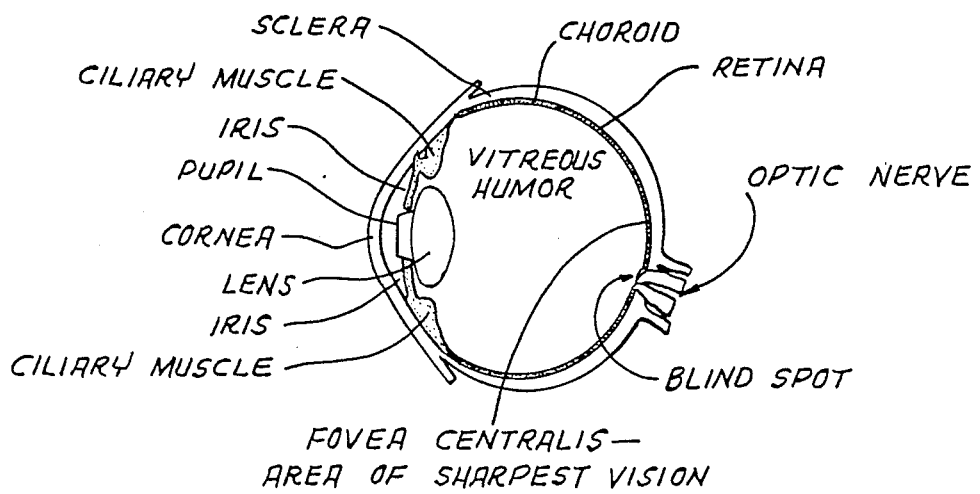
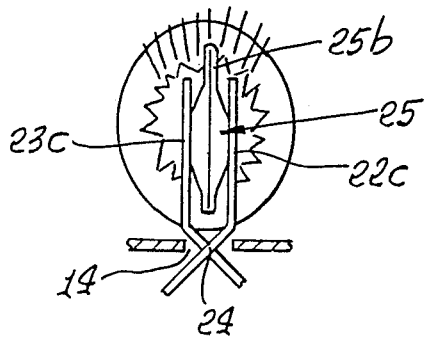
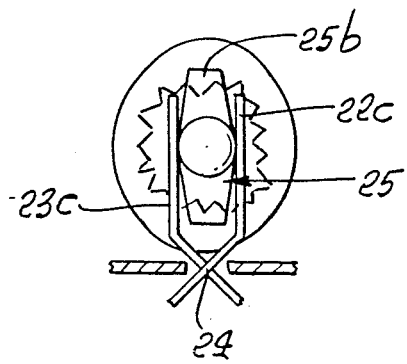

INTRAOCULAR LENS IMPLANTATION

This is a continuation of application Ser. No. 07/042,881, filed Apr. 27, 1987, U.S. Pat. No. 4,813,957.

BACKGROUND OF THE INVENTION

This invention relates generally to intraocular lens implantation, and more particularly concerns apparatus and method for achieving such implementation via a very small surgical incision in the corneo-scleral limbus of the eye.

In the past, forceps have been used with blades that clamp the plastic lens for introducing it into the eye via a relatively wide wound or incision in the corneo-scleral limbus. A typical wound was required to have a width of about 7-15 millimeters in order to pass the forcep blades and to allow spreading of the blades to release the plastic lens in the eye.

Problems encountered included laceration of the elastic silicon lens, and undesirable sudden release and rapid unfolding of the lens (as opposed to gentle release) causing injury to intraocular tissue, due to inability to separate the blades widely and gently. The usual wide incision is undesirable due to the amount of suturing required to close the wound, and time required for such suturing, increased or undesirably long convalenscence time, increase in astigmatic complications, difficulty in preventing collapse of the intraocular chambers during the operation, and increased risk of post-operative complications. Further, plastic lenses could and did at times become captured by the blades of prior forceps, requiring dangerous instrumentation to release the lens from the grasp of such forceps.

SUMMARY OF THE INVENTION

It is a major object of the invention to provide method and apparatus, overcoming the above problems and difficulties. Basically the invention permits wide separation of the blades and gentle release of the folded lense within the eye, while motion is transmitted to the blades via a very narrow incision.

The method involves implanting a plastic lens into the eye lens zone from which a natural but cataractous lens has just been removed (or removed in the past) as via a narrow surgical incision in the corneo-scleral limbus, and while using a forceps having blades projecting from or beyond cross arm portions defining a crossover locus. The method includes the steps:

(a) manipulating the forceps to introduce the blades and clamped plastic lens through the incision and into said zone, and to place the cross arm portions in said incision, (b) further manipulating the forceps to spread the blades thereby releasing the plastic lens to accommodate to said zone, and thereafter relatively closing together the blades while maintaining the cross-fixation arm portions at or proximate said incision, (c) and withdrawing the relatively closed together blades from said zone and via said incision.

Typically, the (b) step is carried out to separate the blades to an extent much wider than the incision; and the blades are, for example, separated within the eye to an extent in excess of 4 mm, and typically between 6-8 mm, the narrow surgical incision having a width less than about 3 mm.

Further, the plastic lens is typically folded and held in elastically folded state, by the blades, while being introduced through the narrow incision; and the blades are slowly and gently spread apart, by pressure on the forceps handles producing motion transmission through the narrow incision, to allow controlled elastic unfolding of the lens for precision interfitting with the eye tissue. Such full excursion blade separation is achieved by force transmission through the cross fixation arm portions which in the wound do not require more than 1 to 2 mm space or size.

Finally, the improved forceps is not only useful as an intraocular lens holder, but also as a utility forceps, capable of passing through a small puncture wound to insert a lens implant, or grasp an intraocular foreign body for its removal or better positioning—all through the small puncture wound.

These and other objects and advantages of the invention, as well as the details of an illustrative embodiment, will be more fully understood from the following specification and drawings, in which:

DRAWING DESCRIPTION

FIG. 13 is enlarged frontal view of a plastic lens of the type to be implanted;

FIG. 14 is a perspective view of the FIG. 13 lens, partially folded;

FIG. 15 is a frontal view of the forceps of the invention with blades holding the plastic lens in folded condition and positioned within the eye, as related to the lens capsule;

FIG. 16 is a view like FIG. 15, after the blades have been separated, showing elastic expansion of the plastic lens between the separated blades, with no remaining dangerous elastic compression, and as dimensionally related to the narrow incision.

FIG. 17 is a schematic view of the eye; and

DETAILED DESCRIPTION

Figure 1:
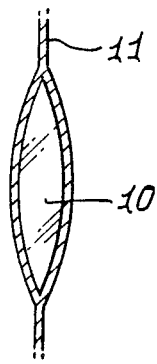
FIG. 1 is a side view of a cataractous opaque lens.
Figure 2:
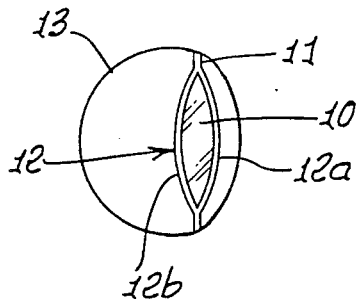
FIG. 2 is a side view of the cataractous opaque lens within the lens capsule in the eye.
Figure 3:
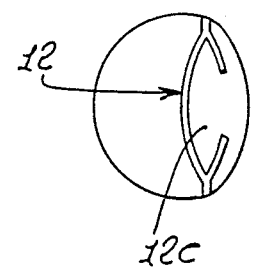
FIG. 3 is a side view of the anterior lens capsule after removal of the opaque cataract lens and the central portion of the anterior capsule.
Figure 4:
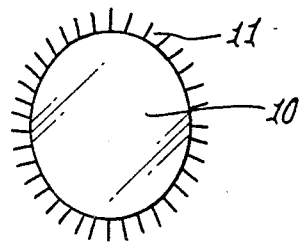
FIG. 4 is a front view of the cataractous lens as seen in FIG. 1, showing zonula fibers holding the capsule.

Referring first to FIGS. 1 and 2, they show, in side view, and schematically, a cataractous opaque lens 10, bounded peripherally by zonula fiber 11, and located between anterior and posterior portions 12a & 12b of the lens capsule. The eye outline appears schematically at 13, and FIG. 17 is a section accurately showing corresponding parts, as well as other parts, of the eye. FIG. 3 shows the capsule void 12c after removal of the cataractous lens tissue. FIG. 4 is a front view of the lens 10 seen in side view in FIG. 1.

Figure 5:
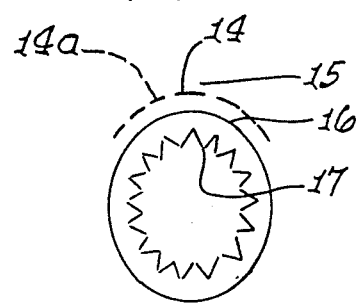
FIG. 5 is a front view showing the location of a surgical 1 to 2 mm incision in the corsoscleral tissue, outwardly from the limbus.

FIG. 5 is a schematic frontal view of the eye, showing a narrow (for example about 3 mm wide) incision or puncture 14 in the corneoscleral tissue 15, at a short distance (as for example about 2 mm) from the limbus 16, the latter designating the merging of light (scelera) and dark (iris periphery) zones of the eye. The present invention makes possible the use of such a narrow, i.e. short, puncture wound, as opposed to the prior very wide incision, indicated by broken lines 14a, which was necessary in order to implant a plastic or silicon lens into the capsula 12. Such a wide (typically 15-18 mm) incision requries much more suturing than is required for the short incision or puncture wound 14, and requires a longer convalescence period, with increased risk of post-operative complications. The cataractous lens is more recently removed by phacoemulsification with ultrasonic vibration fragmentation and aspiration via the puncture 14, leaving jagged anterior "leaves" or serrations 17 in the anterior capsula portion 12a; the posterior capsula portion 12b remains clear. Anterior capsulatomy removes the central anterior capsula, leaving space indicated at 12c in FIG. 3.

Figure 6:
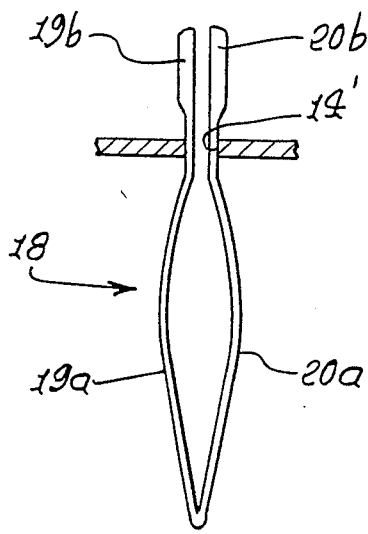
FIG. 6 is a front view showing prior straight forceps with arms and blades whose narrow separation is limited by a 3 mm incision in the corsoscleral limbal tissue.

FIG. 6 shows a straight forceps 18 having an arm 19a continuing forwardly to merge with a blade 19b, and an arm 20a continuing forwardly to merge with a blade 20b. The blades have been inserted through a narrow (3 mm for example) incision as indicated at 14', and that incision characteristically severely limits the separation of the blades to release a plastic or silicon lens clamped between them; for that reason, it was previously considered necessary to form a wide incision, as previously referred to at 14a, in order to release the plastic replacement lens. Such a large wound tends to allow fluid escape from the eye, with impending ocular collapse and damage in the intraocular tissue.

Figure 7:
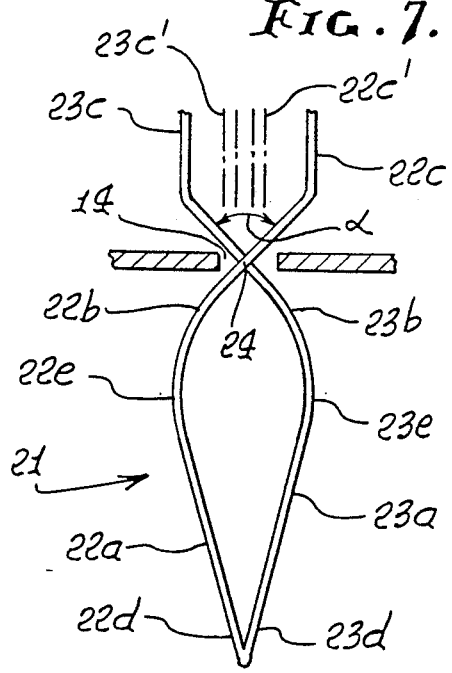
FIG. 7 is a front view showing the forceps of the invention with cross action arm portions passing through the corsoscleral limbal tissue, the forceps blades having been widely separated, i.e. not limited as in FIG. 6.

The forceps of the present invention is shown schematically at 21 in FIG. 7. That forceps is characterized by an arm 22a extending generally forwardly to merge with diagonally rightwardly and forwardly extending cross-over portion 22b, the latter terminating at blade 22c. Similarly, a second arm 23a extends generally forwardly to merge with diagonally leftwardly and forwardly extending cross-over portion 23b, the latter terminating at forwardly extending blades 23c parallel to blade 22c. The blades also extend forwardly relative to the diagonals. Note that the cross-action portions 22b and 22c are laterally displaced and slide adjacent one another by sequence or release manipulation of the forceps arms so that the cross-over point 24 remains in, or very closely proximate to, the puncture locus 14, as during expansion of the blades from their initially inserted broken line positions 22c' and 23c' to their expanded solid line positions 22c and 23c. This then allows a wide degree of such expansion to free the plastic lens within the capsula 12, without restriction imposed by the narrow puncture 14. Arms 22 and 23 defining handles 22e and 23e are typically joined together at their outer ends 22d and 23d.

FIGS. 8-12 show the implantation sequence for an elastic, molded plastic or silicon lens implant 25 as represented in FIG. 13. That lens has an intermediate and bead-like optical portion 25a, and two oppositely extending haptics or tangs 25b and 25c. It is foldable about a lengthwise axis 26, as seen in FIG. 14, so as to be clamped or held between the blades 22c and 23c, as during implantation viewed in FIGS. 8 and 9, and via the narrow (about 3 mm or less) puncture 14. Typical dimensions appear in FIGS. 13 and 14.

Figure 8:
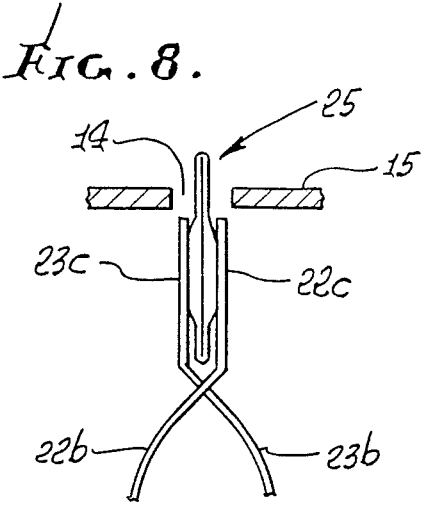
FIGS. 8-12 are sequential views showing steps in the intraocular implantation of a plastic lens, using the forceps of the present invention.
Figure 9:
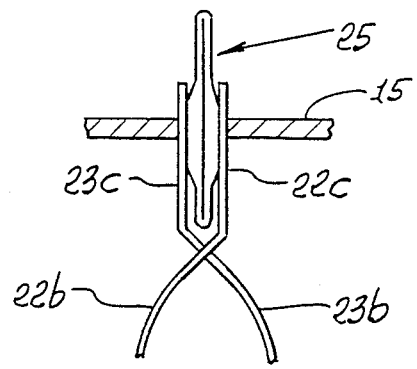
Figure 10:
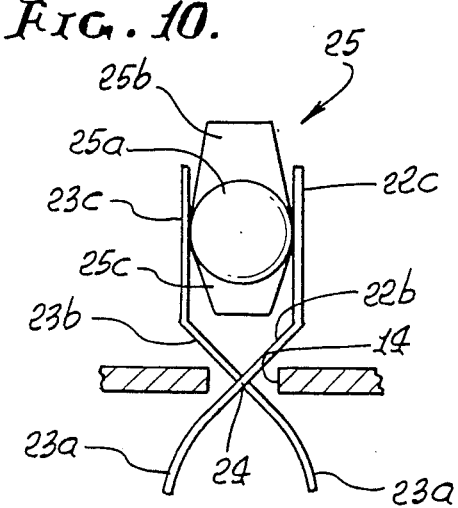

In FIGS. 8 and 9 the arm cross-over (cross-fixation) point or locus 24 is very close to the blades, whereby the blades are held near one another, with the folded lens therebetween, for insertion through the narrow puncture. Once insertion is completed, characterized by location and retention of the forward tang 25b into the tissue bounding the lens cavity or void, as seen in FIG. 15, the blades are allowed to slowly separate as by slow release of manual pressure on the bowed spring arms 22a and 23a of the forceps, and the forceps is also manipulated slightly lengthwise (forward or backward) to maintain the cross-over point 24 in, or proximate, the puncture 14. This allows ultimate wide separation of the blades, to between 4 to 6 mm, as seen in FIGS. 10 and 16, without restriction imposition by the small narrow puncture. The width of the puncture is less than about 3 mm. Note that the cross-over point 24 has moved away from the blades in FIGS. 10 and 11. Angle α defined by the portions 22b and 23b is between 75° and 105°. The blades remain appproximately parallel during their excursions.

Figure 11:
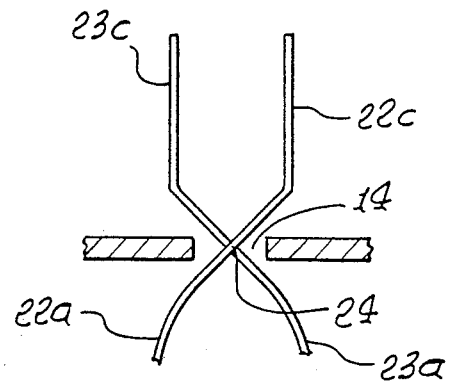
Figure 12:
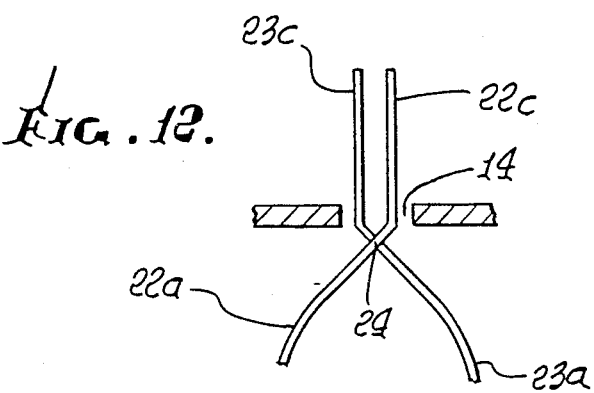

In FIG. 11, the elasticaly expanded (unfolded) artificial lens has dropped away from between the blades, leaving them free for relative closure, as seen in FIG. 12. In the latter, the cross-over point 24 has moved relatively back toward the blades; the blades are closed together and they are positioned for retraction through the puncture.

As referred to above, the forceps of the present invention, has utility, not only as an intraocular lens holder but also as a utility forceps, capable of passing through a small pncture wound to insert a lens implant, or grasp an intraocular foreign body for its removal or better positioning all through the small puncture wound.

The specific angulations of the cross fixation arm portions, their lengths, and the sizes of the two blades, as related to the narrow puncture wound, may vary somewhat depending upon the specific use and functioning of the forceps.

Figure 18:
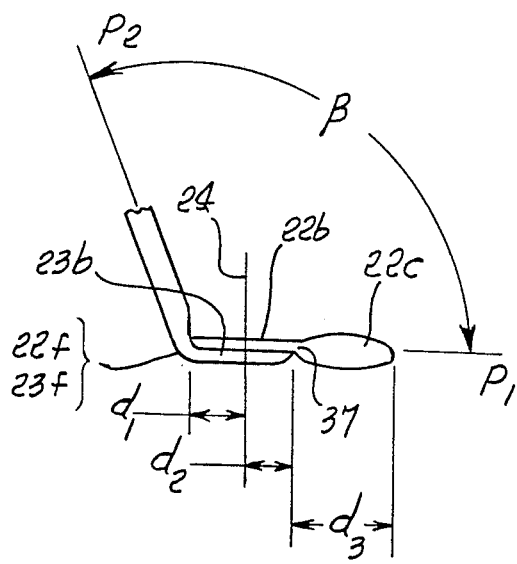
FIGS. 18-20 are views showing modifications.

In FIG. 18, the blades 22c and 23c and the cross over portions 22b and 23b of the arms define a first plane $P_1$ and the remainders of the arms 22a and 23a define a second plane $P_2$. The angle β between $P_1$ and $P_2$ is between 100° and 130°. Arms 22a and 23a join the diagonals at elbows at 22f and 23f. The cross-over locus appears at 24. The dimension $d_1$, 22f to 24 is about 4 mm; the dimension $d_2$ from 24 to the blade inner end 37 is about 3 mm; and the dimension $d_3$, which is the blade length, is about 6 mm.

Figure 19:
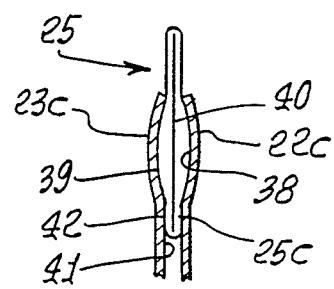

In FIG. 19, each blade 22c and 23c has a shallow concave inner surface 38 to match (or approximately match) the surface convex curvature 39 of the plastic molded lens 25 held folded in half at 40. Each blade also has a second inner surface 41 which is approximately flat to match the flat outer surface 42 of the folded haptic 25c.

Figure 20:
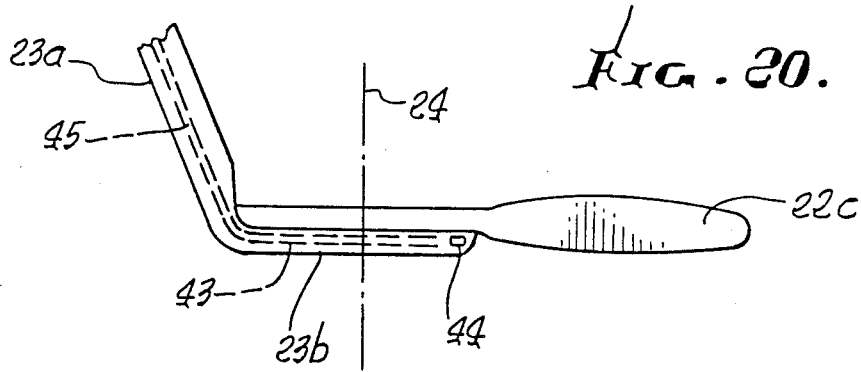

In FIG. 20, at least one of the diagonal portions, such as arm portion 23b, has an interior, lengthwise extending, irrigation channel or cannula 43, for passing eye irrigating liquid to outlet 44, in the eye, when the blades are located in the eye. Passage 45 in arm 23a feeds liquid to channel 43, and under pressure sufficient to keep the anterior and posterior chambers in the eye from collapsing.

I claim:

1. A surgical forceps useful for eye surgery wherein an incision is made in the eye corsocleral tissue, the incision being less than about 3 mm in width, said forceps comprising:
   (a) a first arm extending generally forwardly to merge with a first diagonal portion defined by said arm, said diagonal portion extending forwardly and rightwardly, and a first blade carried by said first diagonal portion,
   (b) a second arm extending generally forwardly to merge with a second diagonal portion defined by the second arm, said second diagonal portion extending forwardly and leftwardly, and a second blade carried by said second diagonal portion,
   (c) said first and second diagonal portions together defining a cross-over locus adapted to be shifted away from the blades as the blades are expanded relatively away from one another in the eye,
   (d) whereby motion may be transmitted from the arms to the blades facilitating expanding of the blades while the cross-over point is maintained in or proximate said incision,
   (e) the overall cross-dimension of the diagonal portions of the arms at the cross-over locus at all times during blade expansion being less than about 3 millimeters,
   (f) the forceps having a first position in which a plastic lens is folded into flattened U-shape and is clamped between the blades, the forceps manipulated to introduce the blades and folded lens through the incision and into an eye lens zone from which a natural lens has been removed, the cross-over locus then located at or closely proximate said incision,
   (g) the forceps having a second position in which the blades are expanded apart wider than the width of the incision, and to an extent in excess of about 7 mm, thereby releasing the plastic lens by unfolding to accommodate to said zone, the cross-over locus at that time maintained located at or proximate said incision,
   (h) the forceps having a third position in which the blades are relatively closed together in said eye zone, with the cross-over locus at that time maintained at or proximate said incision, to accommodate withdrawal of the relatively closed together blades from said zone and via the incision,
   (i) each blade having a concave surface portion to match or approximately match the surface convex curvature of a plastic molded lens, and a second surface portion to match or approximately match the outer surface of a plastic molded lens haptic, and including said plastic lens folded upon itself into U-shape and retained between said blade first portion and second portion,
   (j) said blades extending forwardly relative to said diagonal portions.

2. The forceps, as defined in claim 1 wherein said blades and said diagonal portions of the arms define a first plane, and the remainders of said arms define a second plane, there being an angle $\beta$ between said planes where $\beta$ is between 100° and 130°.

* * * * *